United States Patent [19]

Lernhardt

[11] Patent Number: 5,310,729

[45] Date of Patent: May 10, 1994

[54] INTERFERON-RELATED POLYPEPTIDES AS CR2 LIGANDS AND THEIR USE FOR MODULATING IMMUNE CELL FUNCTIONS

[75] Inventor: Waldemar Lernhardt, Solana Beach, Calif.

[73] Assignee: California Institute of Biological Research, La Jolla, Calif.

[21] Appl. No.: 512,118

[22] Filed: Apr. 20, 1990

[51] Int. Cl.$^5$ .................. A61K 37/00; A61K 37/02; C07K 5/00; C07K 7/00
[52] U.S. Cl. ........................ 514/15; 514/16; 530/327; 530/328
[58] Field of Search ............ 514/15, 14, 16, 13, 514/12; 530/328, 327, 300

[56] References Cited

U.S. PATENT DOCUMENTS 4,801,685 1/1989 Goeddel et al. .................. 530/351
4,966,843 10/1990 McCormick et al. ............ 435/69.51

FOREIGN PATENT DOCUMENTS 8606744 11/1986 PCT Int'l Appl. .......... C12N 15/00
9103251 3/1991 PCT Int'l Appl. .......... A61K 37/02

OTHER PUBLICATIONS

Nemerow et al., Cell, vol. 56, Feb. 10, 1989, pp. 369–377.
Hatzfeld et al., J. Immunol., vol. 140, No. 1, Jan. 1, 1988, pp. 170–175.
Bohnsack et al., J. Immunol., vol. 141, No. 8, Oct. 15, 1988, pp. 2569–2576.
Lambris et al., Proc. Natl. Acad. Sci., USA, vol. 82, Jun. 1985, pp. 4235–4239.
Frade et al., Proc. Natl. Acad. Sci. USA, vol. 82, Mar. 1985, pp. 1490–1493.
Franke et al., *Proc. Natl. Acad. Sci. USA*, 86:4027–4031 (1989).
Lernhardt et al., *Immunol. Rev.*, 99:241–262 (1987).
Melchers et al., *Proc. Natl. Acad. Sci. USA*, 82:7681–7685 (1985).
Servis et al., *J. Immunol.*, 142:2207–2212 (1989).
Tanner et al., *J. Virol.*, 62:4452–4464 (1988).
Weissmann et al., *Prog. Nucl. Acid Res. Mol. Biol.*, 33:251–300 (1986).

*Primary Examiner*—Merrell C. Cashion, Jr.
*Assistant Examiner*—A. M. Davenport
*Attorney, Agent, or Firm*—Thomas Fitting

[57] ABSTRACT

Synthetic polypeptides corresponding to the B lymphocyte CR2 receptor binding site present on an interferon alpha-related CR2 ligand are disclosed together with polypeptide aggregates, compositions, anti-polypeptide antibodies and methods of preparing and using the polypeptides and antibodies.

2 Claims, 3 Drawing Sheets

FIG. 1

```
  1 TGCTCTGTGGGCTGTGTGATCTGCCTCAAACCCACAGCCTGGGTAGCAGGAGGACCTTGATG
                                                                 M   1

61 CTCCTGGCACAGATGAGGAGGAAATCTCTCTCTTTTCTCCCTGCTTGAAGGACAGACATGACTTT
     L   L   A   Q   M   R   R   K   I   S   L   F   S   C   L   K   D   R   H   D   F  21

121 GGATTCCCCAGGAGGAGTTGGCAACCAGTTCCAAAGGCTGAAACCAGCCCTGTCCTC
     G   F   P   Q   E   E   F   G   N   Q   F   Q   K   A   E   T   S   P   V   L  41

181 CATGAGATGATCCAGCAGATCTTCAATCTCTTCAGCACAAAGGACTCATCTGCTGCTTGG
     H   E   M   I   Q   Q   I   F   N   L   F   S   T   K   D   S   S   A   A   W  61

241 GATGAGACCCTCCTAGACAAATTCTACACTGAACTCTACCAGCAGCTGAATGACCTGGAA
     D   E   T   L   L   D   K   F   Y   T   E   L   Y   Q   Q   L   N   D   L   E  81

301 GCCTGTGTGATACAGGGGGTGGGGGTGACAGAGACTCCCCCTGATGAAGGAGGACTCCATT
     A   C   V   I   Q   G   V   G   V   T   E   T   P   L   M   K   E   D   S   I 101

361 CTGGCTGTGAGGAAATACTTCCAAAGAATCACTCTCTATCTGAAAGAGAAGAAATACAGC
     L   A   V   R   K   Y   F   Q   R   I   T   L   Y   L   K   E   K   K   Y   S 121

421 CCTTGTGCCTGGGAGGTTGGCAGAGCAGAAATCATGAGATCTTTTTCTTTGTCAACAAAC
     P   C   A   W   E   V   G   R   A   E   I   M   R   S   F   S   L   S   T   N 141

481 TTGCAAGAAAGTTTAAGAAGTAAGGAATGAAAACTGGTTCAACATGGAAATGATTTTCAT
     L   Q   E   S   L   R   S   K   E                                             150
```

FIG. 2

```
  1 AAGCTTCCCAATTCCTGCCTCGCCACTGTCCTGCCCTCCCAGACATGCTGGGCCCTG
 61 CATGCTGCTGCTGCTGCTGGGCCTGAGGCTACAGCTCTCCCTGGGCATCATCCC
     M   L   L   L   L   L   G   L   R   L   Q   L   S   L   G   I   I   P      25
121 AGTTGAGGAGGAGAACCCCATGGCCCTTGACCTTTGCTTTACTGGTGGCCCTGGGCT
     V   E   E   N   P   M   A   L   T   F   A   L   L   V   A   L   L   G   L    45
181 CAGCTGCAAGTCAAGCTCTGTGTGGCTGTGATCTGCCTCAAACCCACAGCCTGGGTAG
     S   C   K   S   S   C   S   V   G   C   D   L   P   Q   T   H   S   L   G   S  65
241 CAGGAGGACCTTGATGCTCCTGGCACAGATGAGGAAAATCTCTTTTCTCCTGCTTGAA
     R   R   T   L   M   L   L   A   Q   M   R   K   I   S   L   F   S   C   L   K  85
301 GGACAGACATGACTTTGGATTTCCCCAGGAGTTTGGCAACCAGTTCCAAAAGGCTGA
     D   R   H   D   F   G   F   P   Q   E   F   G   N   Q   F   Q   K   A   E    105
361 AACCAGCCCCTGTCCTGCTGTCCATGAGATGATCCAGATCTTCAATCTCTTCAGCACAAAGGA
     T   S   P   V   L   H   E   M   I   Q   I   F   N   L   F   S   T   K   D    125
421 CTCATCTGCTGCTTGGGATGAGACCCTCCTAGACAAATTCTACACTGAACTCTACCAGCA
     S   S   A   A   W   D   E   T   L   L   D   K   F   Y   T   E   L   Y   Q   Q  145
481 GCTGAATGACCTGGAAGCCTGTGTGATACAGGGGGTGACAGAGACTCCCCTGAT
     L   N   D   L   E   A   C   V   I   Q   G   V   G   V   T   E   T   P   L   M  165
541 GAAGGAGGACTCCATTCTGGCCGTGAGGAAATACTTCCAAAGAATCACTCTCTATCTGAA
     K   E   D   S   I   L   A   V   R   K   Y   F   Q   R   I   T   L   Y   L   K  185
601 AGAGAAGAAATACAGCCCTTGTGCCTGGAGGTTGGCAGAGCAGAAATCATGAGATCTTT
     E   K   K   Y   S   P   C   A   W   E   V   G   R   A   E   I   M   R   S   F  205
661 TTCTTTGTCAACAAACTTGCAAGAAAAGTTTAAGAAGTAAGAATGAAAACTGGTTCAACA
     S   L   S   T   N   L   Q   E   S   L   R   S   K   E                          219
```

FIG. 3A

```
     140            142                 152             155
      T    E    L    Y Q  QLNDLEA       C    Y    I    Q
     ACT GAA CTC                        TGT GTA TAC AG
                    469                       504
                                                  508
                                         TGTGG GATCCAG
5' A C T G A G C T C                     ACACC CTAG G
3' T G A C T C G A G                           BamHI
         SacI
```

FIG. 3B

```
      E   L   Y   Q   Q   L   Y   N   V   E   A   C   V
5' ACTGAGCT                                                    GATCCAG
     TGAC TCGAG GAG ATG GTC GAC GTC GAG ATG TTG CAC CTC CGG ACAACTAGGTC
```

INTERFERON-RELATED POLYPEPTIDES AS CR2 LIGANDS AND THEIR USE FOR MODULATING IMMUNE CELL FUNCTIONS

This invention was made with government support under government contract 5 RO1 CS3119 awarded by the National Institutes of Health. The government has certain rights in the invention.

TECHNICAL FIELD

The present invention relates to the CR2 binding region of a CR2 ligand and to polypeptides and polypeptide aggregates that contain the binding region. More particularly, the present invention contemplates CR2 ligand-containing compositions, antibodies to CR2 ligands, rDNA's that express CR2 ligands and methods of using the ligands and the antiligand antibodies.

BACKGROUND OF THE INVENTION

CR2 (CD21) is a cellular receptor on B lymphocytes that is implicated in their growth regulation and is linked to intercellular pathways involved in signaling B cell proliferation. Melchers et al., Nature, 317:264 (1985); Lernhardt et al., Immunol. Rev., 99:239 (1987); Bohnsack et al., J. Immunol., 141:2569 (1988); Cooper et al., Ann. Rev. Immunol., 6:85 (1988); Tedder et al., J. Clin. Immunol., 6:65 (1986); Hatzfeld et al., J. Immunol., 140:170 (1988); Frade et al., Proc. Natl. Acad. Sci. USA, 82:1490 (1985).

CR2 occurs on normal B lymphocytes and on B cell neoplasms. Cooper et al., Ann. Rev. Immunol., 6:85 (1988); Hatzfeld et al., J. Immunol., 140:170 (1988). CR2 functions as a receptor for several complement C3 activation products. The proteolytic C3 activation products iC3b, C3dg and C3d all bind to CR2 and have been shown to mediate both stimulating and inhibiting effects on lymphocytes. Weigle et al., in *Complement*, Muller-Eberhard, H. J. and Miescher, P. A. (eds.), p. 323, Springer-Verlag, Berlin (1985). Because of its central role in B cell function, CR2 function and ligands that modulate that function are of great interest.

The CR2 receptor is also of clinical interest because it is the receptor for the human herpes virus, Epstein-Barr virus. Fingeroth et al., Proc. Natl. Acad. Sci. USA, 86:242 (1989). EBV is the causative agent of infectious mononucleosis, [Henle et al., Proc. Natl. Acad. Sci. USA, 59:94 (1968)] and is possibly a human cancer virus, because it has been linked to nasopharyngeal carcinoma and Burkitt's lymphoma. Henle et al., Science, 157:1064 (1967). In addition, EBV is thought to be associated with x-linked lymphoproliferative disease (Duncan's disease) [Purtillo et al., Lancet i, 935, (1975)] and several human autoimmune disorders. Tosato et al., Adv. Immunol., 37:99 (1985). Lastly, EBV may play a role in the onset of B cell neoplasia observed in a substantial number of patients with AIDS (Yarchoan et al., J. Clin. Invest., 78:439 (1986). In vitro infectious EBV is a T cell-independent B cell stimulator and transforms human B lymphocytes to immortal polyclonal lymphoblastoid cell lines. Cooper et al., Ann. Rev. Immunol., 6:85 (1988). Non-transforming virus is a T cell-dependent B cell activator. Cooper et al., Ann. Rev. Immunol., 6:85 (1988). Drug inhibitors of EBV propagation that operate by interfering with virus binding to CR2 will therefore be of clinical relevance.

Some ligands that bind CR2 have been extensively characterized. For example, the exact sequence motif mediating binding of C3 fragments to CR2 has been elucidated by Lambris et al., Proc. Natl. Acad. Sci. USA, 82:4235 (1985) and has the amino acid residue sequence LYNVEA. Peptides containing this motif have the ability to inhibit aggregated C3d-induced S phase entry of B cells [Lernhardt, et al., Immunol. Rev., 9:239 (1987)] and to inhibit alpha B cell growth factor activity. Melchers, et al., Proc. Natl. Acad. Sci. USA, 82:7681 (1985). However, the precise function of a ligand containing this motif is unclear. Monomeric C3b and C3d are inhibitory, whereas aggregated C3b and C3d stimulate B cell proliferation. Erdei, et al., Eur. J. Immunol., 15:184 (1985); Bohnsack et al., J. Immunol., 141:2569 (1988).

The sequence motif mediating binding of EBV virus to CR2 is present on the gp350/220 protein and has the amino acid residue sequence EDPGFFNVE. Nemerow, et al., Cell, 56:369 (1989).

Although the above reports describe CR ligands and CR2 binding motifs, it is not generally understood that species of interferon also contain unique CR2 binding motifs.

BRIEF SUMMARY OF THE INVENTION

It has now been discovered that CR2 is a receptor for interferon alpha. In addition, a new family of CR2 ligands related to interferon alpha (IFNα) have been discovered that have the capacity to bind CR2 and modulate numerous CR2-mediated events occurring in normal and neoplastic B lymphocytes. This discovery arose when it was determined that polypeptides corresponding to the CR2 binding site present on interferon alpha were identified to have the ability to bind CR2.

Therefore, the present invention describes DNA segments that encode a CR2 ligand and CR2 ligand polypeptides that contain the binding site. Recombinant DNA (rDNA) molecules are also described that contain DNA segments that encode CR2 ligands, as well as rDNA expression vectors capable of expressing CR2 ligands in compatible hosts.

A CR2 ligand comprising a polypeptide is described having as a part of its amino acid residue sequence one or more CR2 binding sites represented by the formula —QLNDLEA— or —QLNNLEA—. In one embodiment a polypeptide aggregate is described having a plurality of polypeptides, each containing one CR2 binding site.

Further contemplated is a hybrid IFNα having a sequence of amino acid residues that form a heterologous CR2 binding site, which sequence is located within the hybrid at a position corresponding to residues 76 to 84 of IFNαA.

Also described are the therapeutic compositions containing CR2 ligands and methods of using those compositions to stimulate or inhibit B lymphocyte proliferation. In particular, inhibitory CR2 ligands containing only one CR2 binding site are described that are useful to inhibit B lymphocyte proliferation, such as in patients with B cell lymphoma. Further, stimulatory CR2 ligands are described that are useful to stimulate B lymphocytes and myelomas, such as in patients with immunodeficiencies or to boost immunoglobulin secretion by hybridoma cultures.

A method of inhibiting infection in vitro or in vivo by Epstein-Barr virus (EBV) is also described in which CR2 ligands are administered to bind CR2 receptor and thereby competitively block EBV infection of host cells by blocking virus binding to the cell receptor, CR2.

Antibody and monoclonal antibody compositions are contemplated that contain antibody molecules that immunoreact with a CR2 ligand of this invention, and more particularly immunoreact a CR2 binding site for CR2.

Diagnostic systems and methods are also described for detecting the presence of CR2 ligand or anti-CR2 ligand antibodies in bodily fluid samples. The described systems and methods utilize the anti-CR2 ligand antibody compositions and CR2 ligands of the present invention.

The present invention provides numerous advantages. For example, a CR2 ligand of the present invention can be used therapeutically as an analog to an IFNα molecule that binds CR2 as described herein and in doing so avoids the side effects normally associated with therapies involving native IFNα, such as nausea, vomiting and diarrhea. In addition, production costs for synthetic polypeptides can be considerably lower than for native IFNα. Other advantages will be apparent to one skilled in the art.

BRIEF DESCRIPTION OF THE DRAWINGS

In the drawings, forming a portion of this disclosure:

FIG. 1 illustrates the nucleotide sequence of a cDNA that codes for interferon alpha strain A (IFNαA), shown from left to right and in the direction of 5' terminus to 3' terminus using the single letter nucleotide base code. The structural gene for the mature IFNαA begins at base 118 and ends at base 567, with the position number of the first base residue in each row indicated to left of the row showing the sequence.

The amino acid residue sequence for IFNαA is indicated by the single letter code below the nucleotide base sequence, with the position number for the last residue in each row indicated to the right of the row showing the amino acid residue sequence. The reading frame is indicated by placement of the deduced amino acid residue sequence below the nucleotide sequence such that the single letter that represents each amino acid is located below the middle base in the corresponding codon. The mature IFNαA protein amino acid residue sequence begins at residue 1 and ends at residue 150.

FIG. 1 also shows the amino acid residue sequence for IFNα88 as compared to the sequence for IFNαA, as indicated by the few single letters below the amino acid residue sequence for IFNαA. Only those residues that differ between IFNα88 and IFNαA are shown, and blank spaces indicate that IFNα88 has the same residue as IFNαA at that residue position.

FIG. 2 illustrates the nucleotide sequence of a DNA segment that codes for a CR2 ligand comprising an alkaline phosphatase-IFNα fusion protein as described in Example 3. The representation of the nucleotide bases, and the corresponding amino acid residues, is shown as described in the legend to FIG. 1 except that the structural gene for the fusion protein begins at base 47 and ends at base 703, and the encoded amino acid residue sequence begins at residue 1 and ends at residue 219.

FIGS. 3A and 3B illustrate the two-step process used in the cassette mutagenesis procedure of Example 4 to produce a hybrid IFNα molecule having a modified CR2 binding site. Step I in FIG. 3A involves creation of Sac1 and BamH1 restriction sites adjacent to the CR2 binding site coding region of rIFNα by site-directed mutagenesis using mismatched primers in a primer extension reaction. Step II in FIG. 3B illustrates the annealing of an oligonucleotide coding for a synthetic polypeptide which includes the amino acid residue sequence —QLYNVEA— to the Sac1/BamH1 digested rIFNα cDNA. The base numbers correspond to the base sequence numbers shown in FIG. 2. By this annealing, a substitution of the previous nucleotide sequence coding a native CR2 binding site with an altered nucleotide sequence results in the formation of a DNA segment coding a hybrid IFNα molecule having a modified CR2 binding site.

DETAILED DESCRIPTION OF THE INVENTION

A. Definitions

Amino Acid Residue: The amino acid residues described herein are preferred to be in the "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature as described in J. Biol. Chem., 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino acid residues or to a amino-terminal NH$_2$ group or to a carboxy-terminal COOH group.

Polypeptide: refers to a linear series of amino acid residues connected to one another by peptide bonds between the alpha-amino group and carboxy group of contiguous amino acid residues.

Protein: refers to a linear series of greater than 50 amino acid residues connected one to the other as in a polypeptide.

Synthetic polypeptide: refers to a chemically produced chain of amino acid residues linked together by peptide bonds that is free of naturally occurring proteins and fragments thereof.

Antibody: The term antibody in its various grammatical forms refers to a composition containing immunoglobulin molecules and/or immunologically active portions of immunoglobulin molecules, i.e., molecules that contain an antibody combining site or paratope.

Antibody Combining Site: An "antibody combining site" is that structural portion of an antibody molecule comprised of heavy and light chain variable and hypervariable regions that specifically binds antigen.

Antibody Molecule: The phrase "antibody molecule" in its various grammatical forms as used herein contemplates both an intact immunoglobulin molecule and an immunologically active portion of an immunoglobulin molecule, referred to also as a fragment of an intact immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v).

Fab and F(ab')$_2$ portions of antibody molecules are prepared by the proteolytic reaction of papain and pepsin, respectively, on substantially intact antibody molecules by methods that are well known. See for example, U.S. Pat. No. 4,342,566 to Theofilopolous and Dixon. Fab' antibody molecule portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred, and is utilized as illustrative herein.

Immunoreaction Conditions: Immunoreaction conditions are those that maintain the immunological activity of the anti-CR2 ligand antibody molecules used in this invention and the CR2 ligand polypeptide sought to be assayed. Those conditions include a temperature range of about 4 degrees C. to about 45 degrees C., preferably about 37 degrees C., a pH value range of about 5 to about 9, preferably about 7 and an ionic strength varying from that of distilled water to that of about one molar sodium chloride, preferably about that of physiological saline. Methods for optimizing such conditions are well known in the art.

Monoclonal Antibody: The phrase "monoclonal antibody" in its various grammatical forms refers to an antibody containing only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and is represented herein by a formula whose left to right orientation is in the conventional direction of 5'-terminus to 3'-terminus.

Polynucleotide: A nucleic acid molecule comprising a polymeric unit of DNA or RNA having a sequence of two or more operatively linked nucleotides that form a single linear strand of nucleotides, also referred to as an oligonucleotide.

Duplex: A double-stranded nucleic acid molecule consisting of two strands of complementary polynucleotide hybridized together by the formation of a hydrogen bond between each of the complementary nucleotides present in a base pair of the duplex. Because the nucleotides that form a base pair can be either a ribonucleotide base or a deoxyribonucleotide base, the term "duplex" referring to either a DNA-DNA duplex comprising two DNA strands, or a RNA-DNA duplex comprising one DNA and one RNA strand.

Base Pair (bp): A partnership of adenine (A) with thymine (T), or of cytosine (C) with guanine (G) in a double stranded DNA duplex.

Nucleic Acid: A term to refer to any of a class of molecules that includes ribonucleic acid (RNA), deoxynucleic acid (DNA) in its single or double stranded forms, and polynucleotides.

DNA segment: A DNA-DNA duplex having a preselected conserved nucleotide sequence and a sequence coding for a CR2 ligand of the present invention.

B. DNA Segments

In living organisms, the amino acid residue sequence of a protein or polypeptide is directly related via the genetic code to the deoxyribonucleic acid (DNA) sequence of the structural gene that codes for the protein and the mRNA from which it is translated. Thus, a nucleotide sequence can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences can code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

An isolated DNA segment of the present invention contains a nucleotide sequence that encodes a CR2 ligand polypeptide sequence of this invention. Typically, the CR2 ligand-encoding DNA segment is no more than about 5,000, and preferably no more than about 2,500, nucleotides in length. Representative nucleotide sequences that encode a CR2 ligand polypeptide of the present invention can include nucleotide sequences that correspond to the nucleotide base sequence shown in FIG. 1 or FIG. 2. A preferred CR2 ligand polypeptide-encoding nucleotide sequence includes a nucleotide sequence that encodes the amino acid residue sequence shown in FIG. 1 from residue 343 to residue 363 corresponding in the amino acid residue sequences for either IFNαA or IFNα88. In a related embodiment, a preferred DNA segment includes a nucleotide sequence that encodes the amino acid residue sequence from residue 1 to residue 219 shown in FIG. 2.

In one embodiment a DNA segment of this invention encodes a hybrid IFNα molecule having a CR2 ligand as described herein. An exemplary DNA segment is described in Example 4.

A DNA segment of the present invention that encodes a CR2 ligand polypeptide can easily be synthesized by chemical techniques, for example, the phosphotriester method of Matteucci, et al., J. Am. Chem. Soc., 103:3185 (1981). Of course, by chemically synthesizing the coding sequence, any desired modifications can be made simply by substituting the appropriate bases for those encoding the native amino acid residue sequence.

C. Recombinant DNA Molecules

The present invention further contemplates a recombinant DNA (rDNA) that includes a DNA segment of the present invention operatively linked to a vector for replication and/or expression. A preferred rDNA is characterized as being capable of directly expressing, in a compatible host, a CR2 ligand of the present invention. By "directly expressing" is meant that the mature polypeptide chain of the expressed CR2 ligand is formed by translation alone as opposed to proteolytic cleavage of two or more terminal amino acid residues from a larger translated precursor protein. An exemplary and preferred rDNA of the present invention is the rDNA molecule pCMV-IFN described in Example 3, and the rDNA molecule pCMV-mIFN described in Example 4.

A rDNA molecule of the present invention can be produced by operatively linking a vector to a DNA segment of the present invention.

As used herein, the term "vector" refers to a nucleic acid molecule capable of transporting between different genetic environments another nucleic acid to which it has been operatively linked. Preferred vectors are those capable of autonomous replication and/or expression of nucleic acids to which they are linked. Vectors capable of directing the expression of genes to which they are operatively linked are referred to herein as "expression vectors". As used herein, the term "operatively linked", in reference to DNA segments, describes that the nucleotide sequence is joined to the vector so that the sequence is under the transcriptional and translation control of the expression vector and can be expressed in a suitable host cell.

The choice of vector to which a CR2 ligand-coding DNA segment is operatively linked depends directly, as is well known in the art, on the functional properties desired, e.g., replication or protein expression, and the host cell to be transformed, these being limitations inherent in the art of constructing recombinant DNA molecules.

In preferred embodiments, the vector utilized includes a procaryotic replicon i.e., a DNA sequence having the ability to direct autonomous replication and maintenance of the recombinant DNA molecule extra chromosomally in a procaryotic host cell, such as a bacterial host cell, transformed therewith. Such replicons are well known in the art. In addition, those embodiments that include a procaryotic replicon also include a gene whose expression confers a selective advantage, such as drug resistance, to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the CR2 ligand-coding segments in a bacterial host cell, such as E. coli transformed therewith. A promoter is an expression control element formed by a DNA sequence that permits binding of RNA polymerase and transcription to occur. Promoter sequences compatible with bacterial hosts are typically provided in plasmid vectors containing convenience restriction sites for insertion of a DNA segment of the present invention. Typical of such vector plasmids are pUC8, pUC9, pBR322, and pBR329 available from BioRad Laboratories, (Richmond, Calif.) and pPL and pKK223 available from Pharmacia, (Piscataway, N.J.).

Expression vectors compatible with eucaryotic cells, preferably those compatible with vertebrate cells, can also be used. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/PML2d (International Biotechnologies, Inc.), and pTDT1 (ATCC, No. 31255).

In preferred embodiments, the eucaryotic cell expression vectors used include a selection marker that is effective in an eucaryotic cell, preferably a drug resistant selection marker. A preferred drug resistance marker is the gene whose expression results in neomycin resistance, i.e., the neomycin phosphotransferase (neo) gene. Southern et al., J. Mol. Appl. Genet., 1:327–341 (1982).

The use of retroviral expression vectors to express the genes of the CR2 ligand-coding DNA segments is also contemplated. As used herein, the term "retroviral expression vector" refers to a DNA molecule that includes a promoter sequences derived from the long terminal repeat (LTR) region of a retrovirus genome.

In preferred embodiments, the expression vector is typically a retroviral expression vector that is preferably replication-incompetent in eucaryotic cells. The construction and use of retroviral vectors has been described by Sorge et al., Mol. Cell. Biol., 4:1730–1737 (1984).

A variety of methods have been developed to operatively link a DNA segment to a vector via complementary cohesive termini. For instance, complementary cohesive termini can be engineered into the CR2 ligand-coding DNA segments during a primer extension reaction by use of an appropriately designed polynucleotide synthesis primer, or by operatively linking a synthetic linker containing one or more restriction sites. Synthetic linkers containing a variety of restriction endonuclease sites are commercially available from a number of sources including International Biotechnologies, Inc., New Haven, Conn. The vector, and DNA segment, if necessary, is cleaved with a restriction endonuclease to produce termini complementary to those of the DNA segment. The complementary cohesive termini of the vector and the DNA segment are then operatively linked (ligated) to produce a unitary double stranded DNA molecule.

The resulting construct is then introduced into an appropriate host to provide amplification and/or expression of the CR2 ligand-coding DNA segments, either separately or in combination. Cellular hosts into which a CR2 ligand-coding DNA segment-containing construct has been introduced are referred to herein as having been "transformed" or as "transformants", and such transformed cells, and cultures of said cells, are also contemplated by the present invention.

The host cell can be either procaryotic or eucaryotic. Bacterial cells are preferred procaryotic host cells and typically are a strain of *E. coli* such as, for example, the *E. coli* strain DH5 available from Bethesda Research Laboratories, Inc., Bethesda, Md. Preferred eucaryotic host cells include yeast and mammalian cells, preferably vertebrate cells such as those from a mouse, rat, monkey or human cell line. Particularly preferred vertebrate host cells include Chinese hamster ovary (CHO) cells available from the ATCC as CCL61 and NIH Swiss mouse embryo cells (NIH/3T3) available from the ATCC as CRL1658.

Transformation of appropriate cell hosts with a recombinant DNA molecule of the present invention is accomplished by methods that typically depend on the type of vector used. With regard to transformation of procaryotic host cells, see, for example, Cohen et al., Proc. Natl. Acad. Sci., USA, 69:2110 (1972); and Maniatis et al., "Molecular Cloning, a Laboratory Manual", Cold Spring Harbor Laboratory, Cold Spring Harbor, N.Y. (1982). With regard to the transformation of vertebrate cells with retroviral vectors containing rDNAs, see for example, Sorge et al., Mol. Cell. Biol., 4:1730-1737 (1984); Graham et al., Virol., 52:456 (1973); and Wigler et al., Proc. Natl. Acad. Sci. USA, 76:1373-1376 (1979).

Successfully transformed cells, i.e., cells containing a CR2 ligand-coding DNA segment operatively linked to a vector, can be identified by well known techniques. For example, cells from a population subjected to transformation with a subject rDNA can be cloned to produce monoclonal colonies. Cells form those colonies can be harvested, lysed and their DNA content examined for the presence of the rDNA using a method such as that described by Southern, J. Mol. Biol., 98:503 (1975) or Berent et al., Biotech., 3:208 (1985).

In addition to directly assaying for the presence of a CR2 ligand-coding DNA segment, successful transformation can be confirmed by methods that detect the expressed CR2 ligand polypeptide. For example, samples of cells suspected of being transformed are assayed for the presence of the CR2 ligand by testing for CR2 ligand binding activity, or by using an antibody that immunoreacts with the CR2 ligand.

D. CR2 Ligands

The present invention contemplates a polypeptide, referred to as a CR2 ligand, capable of specifically binding to the CR2 receptor, as a functional ligand, and thereby effect (modulate) changes in CR2 receptor-containing cell status, such as to induce or inhibit proliferation, to compete with other ligands of CR2 for binding, to inhibit EBV infection, and the like.

A CR ligand is further characterized by the presence of a CR2 binding site. A CR2 ligand of the present invention is one having a CR2 binding site that includes an amino acid residue sequence that corresponds, and is preferably identical, to a sequence represented by the formula —QLNDLEA— or —QLNNLEA—. The overall amino acid residue sequence of a subject CR2 ligand is different from that of native IFNα. A preferred CR2 ligand contains only a single CR2 binding site and has an amino acid residue sequence that is less than about 100 amino acid residues, preferably less than 50, and more preferably less than 20 residues in length.

Additional amino acid residues present on a CR2 ligand in addition to the above indicated sequences can be any residues sequence of residues, but preferably a sequence corresponding to a sequence of an IFNα having a CR2 binding site. IFNα molecules that contain a CR2 binding site are any IFNα molecules having the sequence —QLNDLEA— or —QLNNLEA—, and include the known human IFNα molecules IFNαA (IFNα1), IFNα2, IFNα4a, IFNα4b, IFNα6, IFNα7, IFNα16, IFNα88, IFN (Ovch), IFLrk, LeIF A, LeIF C, LeIF D, LeIF I and the like as described by Weissman et al., Prog. Nucl. Acid Res. Mol. Biol., 33:251-300 (1986).

In a preferred embodiment, a CR2 ligand includes the amino acid residue sequence —QLNDLEA— and corresponds in sequence, and preferably is identical to, a portion of the amino acid residue sequence of IFNαA shown in FIG. 1.

In another embodiment a CR2 ligand includes the amino acid residue sequence —QLNNLEA— and corresponds in sequence, and preferably is identical to, a portion of the amino acid residue sequence of IFNα88 shown in FIG. 1.

Preferred CR2 ligands have an amino acid residue sequence that corresponds, and preferably is identical, to a sequence shown in one of the formulae:

QLNDLEA,
QLNDLEAC,
QLNDLEACV,
QLNDLEACVI,
QLNDLEACVIQ,
QQLNDLEA,
YQQLNDLEA,
LYQQLNDLEA,
QLNNLEA,
QLNNLEAC,
QLNNLEACV,
QLNNLEACVI,
QLNNLEACVIQ,
QQLNNLEA,
YQQLNNLEA, and
LYQQLNNLEA.

Exemplary of the preferred CR2 ligands are the polypeptides shown in Table 1.

TABLE 1

IFN-Related CR2 Ligand Polypeptides

| Polypeptide Designation | Source of Polypeptide Sequence | Amino Acid Residue Sequence |
|---|---|---|
| p1 | IFNα | QLNDLEA |
| p2 | IFNα | QLNDLEACV |
| p3 | IFNα88 | QLNNLEA |
| p4 | IFNα88 | QLNNLEACV |

A subject polypeptide comprising a CR2 ligand includes any polypeptide, analog, fragment or chemical derivative of a polypeptide whose amino acid residue sequence is shown herein so long as the polypeptide is capable of binding CR2 and modulating the function of a CR2-containing cell in a manner disclosed herein. Therefore, a present polypeptide can be subject to various changes, substitutions, insertions, and deletions where such changes provide for certain advantages in its use.

The term "analog" includes any polypeptide having an amino acid residue sequence substantially identical to a sequence specifically shown herein in which one or more residues have been conservatively substituted with a functionally similar residue and which displays the ability of a CR2 ligand as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

Thus additional CR2 ligands contemplated by the present invention have an amino acid residue sequence that corresponds to one of the sequences represented by the formulae:

QNNDVEATS,
QLNDVEATS,
QLNNVEATS,
QLNNLEATS,
QSNGVEALT,
QNSGLEALT,
QNSGLEALI,
QSNGVEALI,
QNSVGEALI,
QNAIVEALI, and
QNAIVEALT.

The phrase "conservative substitution" also includes the use of a chemically derivatized residue in place of a non-derivatized residue provided that such polypeptide displays the requisite binding activity.

The term "fragment" refers to any subject polypeptide having an amino acid residue sequence shorter than that of a polypeptide whose amino acid residue sequence is shown herein.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

Additional modifications of a subject polypeptide are contemplated that are directed to affecting the polypeptide's stability in aqueous solutions, so long as the modifications do not substantially affect the capacity of the polypeptide to otherwise function as intended. In particular, modifications to the amino terminal amino acid residue are contemplated that will inhibit susceptibility to degradation by amino peptidases, such as leucine amino peptidase, that are present in solutions in contact with the polypeptide when in use. Such modifications include acetylation of the amino terminal residue, or the preparation of the amino terminal residue as a desamino residue, lacking a free amino group.

The present invention further includes a composition that includes a subject polypeptide in combination with one or more of a pH buffering agent, wetting agent, anti-oxidant, reducing agent, aqueous medium, and the like, such composition being formulated as an aqueous solution for a use as described herein or as a dry composition, such as a powder, that can be reconstituted to form an aqueous solution.

A subject polypeptide can be prepared using recombinant nucleic acid methodologies well known, some of which are disclosed herein above. For instance, DNA segments that encode a CR2 ligand are prepared and then ligated into an expression vector, and a host transformed therewith can be used to produce the polypeptide. The recombinant expression vectors so formed that are capable of expressing a subject polypeptide and methods of their use for producing a subject polypeptide are contemplated as part of the present invention.

A subject polypeptide can also be prepared using the solid-phase synthetic technique initially described by Merrifield, in J. Am. Chem. Soc. 85:2149–2154 (1963). Other polypeptide synthesis techniques may be found, for example, in M. Bodanszky et al., *Peptide Synthesis*, John Wiley & Sons, 2d Ed., (1976) as well as in other reference works known to those skilled in the art. A summary of polypeptide synthesis techniques may be found in J. Stuart and J. D. Young, *Solid Phase Peptide Synthesis*, Pierce Chemical Company, Rockford, Ill., 3d Ed., Neurath, H. et al., Eds., p. 104–237, Academic Press, New York, N.Y. (1976). Appropriate protective groups for use in such syntheses will be found in the above texts as well as in J. F. W. McOmie, *Protective Groups in Organic Chemistry*, Plenum Press, New York, N.Y. (1973).

In general, those synthetic methods comprise the sequential addition of one or more amino acid residues or suitably protected amino acid residues to a growing polypeptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amid linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence any remaining terminal and side group protecting groups (and solid support) are removed sequentially or concurrently, to provide the final polypeptide.

In another embodiment, a CR2 ligand is characterized by the presence of a plurality of polypeptide segments, each polypeptide segment being defined by the presence of one of the following amino acid residue sequences:

—QLNDLEA—, or
—QLNNLEA—.

The included polypeptide segments can be adjacent and/or contiguous within the polypeptide chain, with adjacent segments being separated in the amino acid residue sequence of the polypeptide by one or more spacing residue. Preferably, the spacing residues make up a spacing segment in the range of about 1 to about 20, preferably about 5 to about 15, and more usually about 10, amino acid residues in length.

In addition, a subject polypeptide can contain a leader segment of 1 conveniently up to about 20, such as about 5, about 10 or about 15, amino acid residues located amino-terminal to the amino-terminal CR2 ligand-derived or spacing segment.

In a similar manner, a subject polypeptide need not end with the carboxy-terminal residue of a CR2 ligand-derived segment or spacer segment. A carboxy terminal tail segment can be present containing 1 conveniently up to about 20, such about 5, about 10 or about 15, amino acid residues.

Preferred polypeptides of the present invention having a plurality of segments are defined by the formula:

B—(X$_n$—QLNULEA—Z$_m$)$_a$—J, the above formula, B is an amino-terminal NH$_2$ group or a previously discussed leader segment; J is a carboxy-terminal COOH group or a previously discussed tail segment; X and Z are first and second, respectively, spacing segments whose amino acid residue sequences can be the same or different; U can be either aspartic acid (D) or asparagine (N) in each amino acid residue sequence in parenthesis; n is either 1 or 0 such that when n is 1, X is present, and when n is 0, X is not present; m is either 1 or 0 such that when m is 1, Z is present, and when m is 0, Z is not present; and a is an integer from 2 to about 10, more preferably 2 to about 5 and usually 2 to 3, indicating the number of times the amino acid residue sequence in parenthesis is present (repeated) in the polypeptide primary structure. Preferably, the sequence in parenthesis corresponds in its entirety, and preferably is identical to, a portion of the amino acid residue sequence of CR2 ligand shown in FIG. 1 or FIG. 2.

In another embodiment, a CR2 ligand is contemplated in which the included CR2 ligand polypeptides described above are present as a conjugate comprised of a plurality of said polypeptides operatively linked, by other than a peptide bond between the alpha-amino group and carboxy group of contiguous amino acid residues, where at least two of the linked polypeptides have an amino acid residue sequence corresponding to that represented by the formula:

B—(X$_n$—QLNULEA—Z$_m$)$_a$—J, wherein B, X, Z, J, n, m and a are defined as previously discussed except that a can also be the integer 1.

In preferred embodiments, a conjugate of this invention has a molecular weight of less than about 40,000 daltons, preferably less than about 20,000 daltons, and more preferably less than about 10,000 daltons. Typically, a subject conjugate has a molecular weight of no more than about 15,000 daltons, preferably no more than about 8,000 daltons, and usually no more than about 4,000 daltons. Preferably, the conjugate is dimeric or trimeric, i.e., consists essentially of two or three polypeptide chains, respectively.

A polypeptide conjugate of this invention is further characterized by its ability to bind CR2 receptor and thereby modulate CR2 containing cells as disclosed herein.

The techniques of polypeptide conjugation or coupling through activated functional groups presently known in the art are particularly applicable. See, for example, Aurameas, et al., Scand. J. Immunol., 1:7-23 (1978), and U.S. Pat. Nos. 4,493,795, 3,791,932 and 3,839,153. In addition, a site directed coupling reaction can be carried out so that any loss of activity due to polypeptide orientation after coupling can be minimized. See, for example, Rodwell, et al., Biotech., 3:889-894 (1985), and U.S. Pat. No. 4,671,958.

One or more additional amino acid residues may be added to the amino- or carboxy- termini of the polypeptide to assist in linking two or more polypeptides to form a conjugate. A preferred method of linking is to form a disulfide bridge between two polypeptides that each have at least one cysteine residue, said bridge formed by exposure of the polypeptides to oxidizing conditions. One preferred linking method involves air-oxidation of cysteine residues present on CR2 ligands in solution. Exemplary is the air-oxidation of rIFNα protein described in Example 3d, in which each rIFNα protein has a single CR2 binding site that, upon oxidation, forms a CR2 ligand having more than two CR2 binding sites.

Where the polypeptide to be linked is a synthetic polypeptide, a cysteine residue can be incorporated into the amino acid residue sequence providing the capacity for disulfide bridges therein. Preferably, the cysteine residue can be introduced at one or both termini of the polypeptide such that the aggregate formed upon oxidation is a dimer or multimer, respectively, of the cysteine-containing polypeptide, having end-to-end linkages at each termini containing a cysteine residue.

E. Hybrid IFNα Molecules and Compositions

The present invention also contemplates a hybrid interferon alpha (hybrid IFNα) molecule that comprises an IFNα molecule having a heterologous CR2 binding site.

Human IFNα molecules are known to represent a family of proteins that are related by having homology in their amino acid residue sequences, and yet are distinct species based on their specific amino acid residue sequences and their biological activity. By the present discovery that CR2 binding sites are present within species of IFNα, one can alter the CR2 binding specificity and binding affinity of an IFNα molecule by substituting a heterologous CR2 binding site for the region of an IFNα molecule corresponding to amino acid residues 76 to 84 of IFNαA shown in FIG. 1.

In cases where the hybrid IFNα molecule contains a CR2 binding site that increases the binding affinity with CR2, the hybrid IFNα molecule can be used effectively at lower concentrations as compared to the native IFNα counterpart. Reduced dosages provide the advantage that the administered patient is subjected to less side effects associated with IFNα therapies.

A heterologous CR2 binding site, as used herein, refers to a sequence of amino acid residues present in a CR2 ligand that (1) have the capacity to bind to CR2 and function as a CR2 ligand, and (2) are not found naturally in the CR2 ligand.

Thus, a hybrid IFNα is comprised of two parts, a heterologous CR2 binding site and the non-CR2 binding site portion of the IFNα molecule. Stated differently, a hybrid IFNα is an IFNα molecule having a modified CR2 binding site, such that the modification produces an altered amino acid residue sequence within the CR2 binding site, which altered sequence is not normally found in the IFNα molecule.

Any CR2 binding site can be a heterologous CR2 binding site, so long as it is substituted into an IFNα molecule other than the IFNα species in which the CR2 binding site is found in nature.

Representative CR2 binding sites suitable for use as heterologous CR2 binding sites include the binding sites defined by the IFNα-related CR2 ligands of the present invention, shown in Table 1, by the CR2 ligands p7, p8 and p9 in Table 2 derived from complement C3 or from CR2 binding protein (CBP), and by the CR2 binding sequence of EBV's gp350/220 protein, including conservative substitutions thereof.

Preferred heterologous CR2 binding site containing amino acid residue sequences suitable for use in a hybrid IFNα molecule are represented by a formula selected from the group consisting of:

QLNDLEACV,
QNNDLEACV,
QLYNVEATS,
QNNDVEATS,
QLNDVEATS,
QLNNVEATS,
QLNNLEATS,
QLYNVEACV,
QNSGVEALI, and
KPAIVEAGG.

An IFNα molecule suitable for use in producing a hybrid IFNα molecule can be any IFNα. Numerous IFNα species have been identified whose nucleotide sequences are known, including the IFNα species identified by the designation IFNαZ, where Z is A, 1, 2, 4a, 4b, 5, 6, 7, 8, 16, 88, ;LeIF X, where X is A, B, C, D, F, G, H, I, J and the like. See Weismann et al., *Prog. Nucl. Acid Res. Mol. Biol.*, 33:251-300, 1986, for descriptions of the above IFNα species, including their nucleotide sequences.

The methods for producing a hybrid IFNα molecule include the recombinant nucleic acid methodologies described herein, and particularly by modification of existing rDNA molecules in the nucleotide base portion that encode a CR2 binding site as to encode a modified (heterologous) CR2 binding site. Methods for modifying a rDNA to encode a modified CR2 binding site can include (1) substitutions of small DNA segments that encode a modified CR2 binding site into a larger DNA segment encoding an IFNα molecule, referred to as cassette mutagenesis, and (2) site-directed mutagenesis using mismatched primer extension reactions. Both of these methods are described in Example 4 to produce the exemplary hybrid IFNα, designated pCMV-mIFNα, having a modified (heterologous) CR2 binding site.

F. Therapeutic Compositions and Methods

Therapeutic compositions of the present invention contain a physiologically tolerable carrier together with a CR2 ligand, a CR2 polypeptide conjugate, or a polyclonal or monoclonal anti-CR2 ligand antibody, as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

Methods of Modulating the Function of CR2-Containing Cells

Methods for modulating the function of CR2-containing cells in vivo or in vitro are contemplated by the present invention.

It has been discovered that species of interferon alpha (IFNα), namely INFαA, IFNα88 and the like, contain a CR2 binding site.

The CR2 ligands of the present invention also contain a CR2 binding site, are related to IFNαA or IFNα88, and therefore are useful as analogs of interferon to the extent that these interferons exert their action by complexing with (binding) CR2.

It has also been discovered that CR2 ligands have the capacity to induce (modulate) changes in the present status of a CR2-containing cell, such as normal or neoplastic B lymphocytes. In addition, the CR2 ligands exhibit the modulating capacity on B lymphocytes from mammals such as mice, sheep, cattle, horses, and man. These changes include stimulation or inhibition of proliferation of the lymphocyte. The capacity of a CR2 ligand to inhibit, as compared to the capacity to stimulate, B lymphocytes depends on the structure of the ligand, and particularly on the number of CR2 binding sites, and their relative spacing in the CR2 ligand.

The inhibitory or stimulatory capacity of a CR2 ligand of the present invention can be readily determined by a variety of methods, such as by monitoring changes in the amount of thymidine uptake by cultured B lymphocytes in the presence of various amounts of CR2 ligand, as disclosed in Example 8.

A CR2 ligand is inhibitory if it contains only one CR2 binding site. A CR2 binding site present in a CR2 ligand of the present invention has an amino acid residue sequence that corresponds, and is preferably identical, to a sequence represented by the formula —QLNDLEA— or —QLNNLEA—.

Representative inhibitory CR2 ligands are the polypeptides:

QLNDLEA,
QLNDLEAC,
QLNDLEACV,
QLNDLEACVI,
QLNDLEACVIQ,
QQLNDLEA,
YQQLNDLEA,
LYQQLNDLEA,
QLNNLEA,
QLNNLEAC,
QLNNLEACV,
QLNNLEACVI,
QLNNLEACVIQ,
QQLNNLEA,
YQQLNNLEA,
LYQQLNNLEA,
QNNDVEATS,
QLNDVEATS,
QLNNVEATS,
QLNNLEATS,
QSNGVEALT,
QNSGLEALT,
QNSGLEALI,
QSNGVEALI,
QNSVGEALI,
QNAIVEALI, and
QNAIVEALT.

Thus, in one embodiment the present invention provides for a method of inhibiting CR2 function on CR2-containing cells and comprises administering to a mammal a therapeutically effective amount of a physiologically tolerable composition containing an inhibitory CR2 ligand, thereby forming. A competition reaction admixture in the mammal wherein the inhibitory CR2 ligand competes with native CR2 ligands for binding with the CR2. The inhibitory CR2 ligand is administered to the mammal in a predetermined amount calculated to achieve the desired effect, i.e., in a therapeutically effective amount.

For instance, when used as an agent for inhibiting B lymphocyte proliferation, such as in a human patient displaying the symptoms of an autoimmune disease or in a patient with B cell lymphoma, the inhibitory CR2 ligand is administered in an amount sufficient to achieve a plasma concentration of from about 0.1 ug/ml to about 100 ug/ml, preferably from about 1.0 ug/ml to about 50 ug/ml, more preferably at least about 2 ug/ml and usually 5 to 10 ug/ml.

In another embodiment, the present invention provides for a method of stimulating proliferation of a CR2-containing cell, particularly a B lymphocyte in, for example, a human exhibiting B cell immunodeficiencies, a B cell hybridoma cell line in culture to boost production of antibody molecules, and the like.

Thus, the present invention contemplates a method of in vivo stimulating CR2-containing cells in a mammal that comprises administering a therapeutically effective amount of a physiologically tolerable composition containing a stimulatory CR2 ligand to a mammal in a predetermined amount calculated to achieve the desired effect.

A stimulating CR2 ligand is one having at least two CR2 binding sites, wherein each binding site has an amino acid residue sequence that corresponds, and is preferably identical, to a sequence represented by the formula —QLNDLEA— or —QLNNLEA—. Preferred are the CR2 ligands described herein having a plurality of CR2 binding sites, and the rIFNα protein compositions described herein having at least two CR2 binding sites.

In preferred embodiments, a stimulating CR2 ligand has the CR2 binding sites positioned in the ligand such that the binding sites as defined by the formulas immediately above are separated by about 10 to about 150 amino acid residues, preferably about 60 to 100 residues, and more preferably about 80 amino acid residues.

When used as an agent to in vivo stimulate B lymphocyte proliferation, such as in a human displaying B cell immunodeficiencies, the stimulatory CR2 ligand is administered in an amount sufficient to achieve a plasma concentration of from about 0.01 ug/ml to about 100 ug/ml, preferably from about 1.0 ug/ml to about 50 ug/ml, more preferably at least about 2 ug/ml and usually 5 to 10 ug/ml.

A representative stimulatory CR2 ligand is the rIFNα protein composition having two CR2 binding sites as described in Example 3d.

The present invention also contemplates a method of in vitro stimulating B cell hybridoma cells in culture. A culture of B cell hybridoma cells is admixed with an effective amount of a stimulatory CR2 ligand and maintained under culture conditions for a time period sufficient to allow the admixed ligand to specifically bind any CR2 receptor present in the culture. An effective amount is that amount which produces a concentration of ligand in the culture sufficient to bind essentially all of the CR2 receptor present, and usually is at a concentration of about 0.01 ug to about 1 mg per ml preferably 0.1 ug to 50 ug, more preferably 1 to 10 ug/ml.

It has also been discovered that antibodies directed against a CR2 binding site have the capacity to indirectly inhibit CR2 function by immunoreacting with CR2 ligands such as IFNα and thereby interfering with the CR2 ligand's ability to bind CR2. Therefore, anti-CR2 ligand antibody molecules that immunoreact with either of the CR2 ligand polypeptides QLNDLEACV or QLNNLEACV, and compositions containing those molecules, can be used in a method for inhibiting CR2 function, including the inhibition of B lymphocyte proliferation and other cellular responses that occur as a result of IFNα binding to CR2.

Thus, in this related embodiment for inhibiting CR2 function, the physiologically tolerable composition administered contains a therapeutically effective amount of an anti-CR2 ligand antibody molecule of this invention in an amount sufficient to immunoreact with the CR2 ligand present in the patient, thereby competing with native CR2 ligand for binding to CR2 and inhibiting normal CR2 ligand-induced CR2 functions.

For example, the anti-CR2 ligand antibody molecules can be administered to block IFNα function by immunoreacting with the CR2 binding site present on IFNα, thereby preventing normal IFNα binding to its target, the CR2 receptor.

An effective amount of therapeutic antibody is that amount which produces a concentration of antibody sufficient to immunoreact with essentially all of the CR2 receptor present on available B lymphocytes of the administered patient, and usually is in the order of about 0.01 to 10, preferably one to several milligrams of active ingredient per kilogram bodyweight of individual per day, depending on the route of administration.

Insofar as stimulatory CR2 ligands have the capacity to stimulate in vivo proliferation for CR2-containing cells as disclosed herein above, the present invention also contemplates the in vivo use of anti-CR2 antibody molecules to inhibit CR2 ligand induced proliferation of CR2 containing cells.

In a related embodiment, the anti-CR2 ligand antibody molecules can be used as an antidote to therapies in which a CR2 ligand, such as IFNα, is administered first to modulate CR2 function, and the antidote is thereafter administered to neutralize the modulating effect of therapeutically administered CR2 ligands. The choice of anti-CR2 ligand antibody to be administered as an antidote depends on the CR2 ligand to be neutralized, and requires that the administered antibody (antidote) have the capacity to immunoreact with the CR2 ligand.

The therapeutic compositions containing CR2 ligand or anti-CR2 ligand antibody molecules are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As an aid to the administration of effective amounts of CR2 ligand, a diagnostic method of this invention for detecting CR2 ligand in the subject's blood is useful to characterize the fate of the administered ligand.

2. Methods of Inhibition and Treatment of Epstein-Barr Virus Infection

Epstein-Barr virus (EBV) infection of mammalian cells in an aqueous suspension, such as blood, is inhibited by methods of the present invention.

An aqueous suspension containing mammalian cells having a CR2 receptor thereon, such as B lymphocytes, is admixed with a therapeutically effective amount of a physiologically tolerable composition of CR2 ligand of the present invention and maintained for a time period sufficient to allow the CR2 ligand polypeptides of the composition to specifically bind any CR2 receptor present in the suspension. When the admixture contains a concentration of EBV that is sufficient to infect the mammalian cells under normal physiological conditions when no pharmacological intervention or treatment is undertaken, the therapeutically effective amount of the CR2 ligand-containing composition utilized in this method is that which produces a concentration of CR2 ligand in the aqueous suspension sufficient to bind essentially all of the CR2 receptor present, and usually is at a concentration of about 1 ug to about 1 mg per ml preferably about 10 ug/ml.

When the method of treatment of the present invention is utilized to inhibit EBV infection in vivo the therapeutically effective amount of the therapeutic composition administered is that which produces a blood concentration of CR2 ligand sufficient to specifically bind the CR2 receptor present and available for EBV infection. Such a blood concentration is usually about 1 ug to about 1 mg of CR2 ligand per ml, and preferably about 10 ug/ml. It is contemplated that multiple administrations of the therapeutic composition of this invention over an appropriate time period and at a dosage level determined by a medical practitioner for the patient will be undertaken for the inhibition of EBV infection in a human patient. Typically, a CR2 ligand is administered substantially concurrently with either recurrence of infection in a chronically infected patient or upon initial exposure to EBV, such as on receipt of tissue from an EBV-seropositive donor. Alternatively, a CR2 ligand can be administered therapeutically to cure or ameliorate diseases in which EBV, or spread of infection, plays a role, such as mononucleosis, Burkitt's lymphoma and nasopharyngeal carcinoma.

Insofar as a method for inhibition or treatment of EBV infection is described, a CR2 ligand suitable for use in the method is any of the several forms of CR2 ligand described herein, so long as it contains at least one CR2 binding site and therefore has the capacity to specifically bind CR2 and thereby compete with EBV for binding.

As used herein, the terms "specifically bind", and "specifically attach", and grammatical forms thereof are used interchangeably and refer to non-random ligand binding, such as that which occurs between CR2 ligand and CR2.

In a related embodiment, a method of inhibiting EBV infection is contemplated that comprises admixing CR2 receptor-containing cells with anti-CR2 ligand antibody molecules. The method is practiced in the manner described above where CR2 ligand is used to inhibit EBV infection, except that the anti-CR2 ligand antibody molecules are substituted for CR2 ligand. The mechanism of inhibiting action depends, however, on the ability of anti-CR2 ligand antibodies to immunoreact (bind) with a CR2 ligand such as the gp350/220 envelope protein on EBV and thereby block the ability to the CR2 ligand to bind the CR2 receptor on the target cell's surface.

Thus in the context of the method using anti-CR2 ligand antibodies to inhibit EBV infection, the terms "specifically bind" and "specifically attach" refer to non-random immunoreaction that occurs between CR2 ligands, such as the EBV gp350/220 protein, and anti-CR2 ligand antibodies of this invention.

In the method of treatment of the present invention, a pharmacological composition, as described above, is administered to a patient in any manner that will efficaciously inhibit the infection of mammalian cells, such as B lymphocytes, by EBV. Preferably, the composition is administered by either intravenous injection of a unit dosage or continuous intravenous infusion of a predetermined concentration of a CR2 ligand or an anti-CR2 ligand antibody of the present invention to a patient in amounts described above for methods to therapeutically bind and effect CR2 function.

G. Antibody Compositions

An antibody of the present invention is a composition containing antibody molecules that immunoreact with a CR2 ligand of the present invention (anti-CR2 ligand antibody molecules). A preferred antibody contains antibody molecules that immunoreact with a polypeptide having an amino acid residue sequence represented by the formula —QLNDLEA— or —QLNNLEA—, and more preferably immunoreact with a polypeptide having the sequence shown by the formula QLNDLEACV or QLNNLEACV.

In addition, it is preferred that anti-CR2 ligand antibody molecules do not immunoreact with a polypeptide having an amino acid residue sequence represented by the formula KFSTELYQ.

An antibody of the present invention is typically produced by immunizing a mammal with an inoculum containing a CR2 ligand and thereby induce in the mammal antibody molecules having immunospecificity for CR2 ligand. The antibody molecules are then collected from the mammal and isolated to the extent desired by well known techniques such as, for example, by using DEAE Sephadex to obtain the IgG fraction.

To enhance the specificity of the antibody, the antibodies may be purified by immunoaffinity chromatography using solid phase-affixed immunizing CR2 ligand. The antibody is contacted with the solid phase-affixed CR2 ligand for a period of time sufficient for the CR2 ligand to immunoreact with the antibody molecules to form a solid phase-affixed immunocomplex. The bound antibodies are separated from the complex by standard techniques.

The antibody so produced can be used, inter alia, in the diagnostic methods and systems of the present invention to detect CR2 ligand present in a body sample, and in the therapeutic methods and systems to inhibit CR2 ligand function.

The word "inoculum" in its various grammatical forms is used herein to describe a composition containing a CR2 ligand of this invention as an active ingredient used for the preparation of antibodies against CR2 ligands. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, dialdehydes such as glutaraldehyde, Klipstein, et al., J. Infect. Dis., 147:318–326 (1983) and the like, or the use of carbodiimide technology as in the use of a water-soluble carbodiimide to form amide links to the carrier. For a review of protein conjugation or coupling through activated functional groups, see Aurameas, et al., Scand. J. Immunol., 1:7–23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen as is well known in the art. Inocula typically contain polypeptide concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

A monoclonal antibody is also contemplated by the present invention and is composed of monoclonal antibody molecules that immunoreact with a CR2 ligand of the present invention. Preferably, the monoclonal antibody molecules immunoreact with a polypeptide having an amino acid residue sequence represented by the formula —QLNDLEA— or —QLNNLEA—, and more preferably represented by the formula —QLNDLEACV— or QLNNLEACV—, but do not immunoreact with a polypeptide having an amino acid residue sequence represented by the formula KFSTELYQ.

antibodies of this invention can be used in the same manner as disclosed herein for antibodies of the present invention.

A monoclonal antibody is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. The preparation of such antibodies were first described by Kohler and Milstein, *Nature* 256:495-497 (1975), which description is incorporated by reference. The hybridoma supernates so prepared can be screened for immunoreactivity with a CR2 ligand or for inhibition of binding of CR2 ligand to CR2. Other methods of producing monoclonal antibodies, the hybridoma cell, and hybridoma cell cultures are also well known.

See, for example, the method of isolating monoclonal antibodies from an immunological repertoire as described by Sastry, et al., *Proc. Natl. Acad. Sci.*, 86:5728-5732 (1989); and Huse et al., *Science*, 246:1275-1281 (1989).

Also contemplated by this invention is the hybridoma cell, and cultures containing a hybridoma cell that produce a monoclonal antibody of this invention.

H. Diagnostic Systems and Methods

1. Diagnostic Systems

A diagnostic system in kit form of the present invention includes, in an amount sufficient for at least one assay, a CR2 ligand and/or an anti-CR2 ligand antibody or monoclonal antibody of the present invention, as a separately packaged reagent. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for the presence of or to quantitate anti-CR2 ligand antibodies in a sample, such as blood, plasma or serum, comprises a package containing at least one CR2 ligand of this invention. In another embodiment, a diagnostic system of the present invention for assaying for the presence or amount of CR2 ligand in a sample comprises a package containing an anti-CR2 ligand antibody composition of this invention.

In preferred embodiments, a diagnostic system of the present invention further includes a label or indicating means capable of signaling the formation of an immunocomplex comprised of either a CR2 ligand of this invention specifically bound to anti-CR2 ligand antibody molecules or an anti-CR2 ligand antibody molecule of this invention specifically bound to a CR2 ligand.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an antibody molecule that is part of an antibody or monoclonal antibody used in the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The label can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanite (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189-231 (1982), which is incorporated herein by reference.

In preferred embodiments, the label is an enzyme, such as horseradish peroxidase (HRP), glucose oxidase, alkaline phosphatase or the like. In such cases where the principal label is an enzyme such as HRP or glucose oxidase, additional reagents are required to visualize the fact that a antibody-antigen complex (immunoreactant) has formed. Such additional reagents for HRP include hydrogen peroxide and an oxidation dye precursor such as diaminobenzidine. An additional reagent useful with HRP is 2,2'-azino-di(3-ethyl-benzthiazoline-6-sulfonic acid) (ABTS).

Radioactive elements are also useful labeling agents and are used illustratively herein. An exemplary radia solid phase, as disclosed for the diagnostic systems herein.

Biological assay conditions are those that maintain the biological activity of the CR2 ligand molecules and the anti-CR2 antibodies in the immunoreaction admixture. Those conditions include a temperature range of about 4° C. to about 45° C., preferably about 37° C., a pH value range of about 5 to about 9, preferably about 7, and an ionic strength varying from that of distilled water to that of about one molar sodium chloride, preferably about that of physiological saline. Methods for optimizing such conditions are well known in the art.

Also contemplated are immunological assays capable of detecting the presence of immunoreaction product formation without the use of a label. Such methods employ a "detection means", which means are themselves well-known in clinical diagnostic chemistry and constitute a part of this invention only insofar as they are utilized with otherwise novel polypeptides, methods and systems. Exemplary detection means include methods known as biosensors and include biosensing methods based on detecting changes in the reflectivity of a surface, changes in the absorption of an evanescent wave by optical fibers or changes in the propagation of surface acoustical waves.

EXAMPLES

The following examples are given for illustrative purposes only and do not in any way limit the scope of the invention.

1. Synthetic Polypeptides

Synthetic polypeptides having amino acid residue sequences that correspond to the formulae shown in Table 1 were obtained from Multiple Peptide Systems (La Jolla, Calif.) after their synthesis by the classical solid-phase technique described by Merrifield, Adv. Enzymol., 32:221–96 (1969). Additional polypeptides having the amino acid residue sequences shown in Table 2 below were similarly prepared.

TABLE 2

| | Synthetic Polypeptides | |
|---|---|---|
| Polypeptide Designation | Source of Polypeptide Sequence | Amino Acid Residue Sequence |
| p5 | IFNα14 | QMNDLEACV |
| p6 | IFNαF (LeiF-F) | QLNDMEACV |
| p7 | C3 | QLYNVEATS |
| p8 | CBP-A | QNSGVEALI |
| p9 | CBP-B | KPAIVEAGG |
| p10 | Fibronectin | SPGRGD |
| p11 | Fibronectin | GRGDSP |

2. Preparation of CR2

CR2 is isolated from Raji cells (ATTC CCL 86) according to the method of Nemerow et al., J. Virol., 58:709–712 (1986). Briefly, Raji cells were lysed in 1 mM NaHCO$_3$, pH 8.0, 2 mM CaCl$_2$ and centrifuged at 300 g to remove nuclei. The resulting 300 g supernatant was collected, adjusted to isotonicity by the addition of NaCl, and then centrifuged at 27,000 g for 30 minutes to form a pellet comprising a crude plasma membrane fraction. The crude plasma membrane fraction pellet was resuspended in solubilizing buffer [phosphate buffered saline (PBS) containing 10% glycerol, 1% NP40 and protease inhibitors], the resuspended material was then maintained at 4 degrees C. (4C) for 60 minutes. The resuspended materials were then centrifuged at 10,000 g for 15 minutes to separate the insoluble materials and the resulting supernatant was collected and diluted to 0.5% NP40. CR2 was purified from the NP40-diluted supernatant by affinity chromatography in a column format using a mixture of anti-CR2 monoclonal antibodies [OKB-7 (Ortho-Immune, Rariton, N.J.) and HB5 (Becton Dickinson, Cockeysville, Md.)] covalently bound to Affi-Gel 10 beads (BioRad, Richmond, Calif.). Bound proteins were eluted in 50 mM diethylamine, pH 11.2, 0.1% Triton X-100 and the eluant was collected. After rapid neutralization of the eluant to a neutral pH, a second chromatography was performed by re-applying the eluted proteins to a second affinity column containing the OKB-7 and HB5 monoclonal antibodies. Proteins eluted from the second chromatography were dialyzed against PBS containing 0.1% Triton X-100 and stored at −80C. The resulting twice affinity purified protein composition contained homogeneous CR2 as assessed by polyacrylamide gel electrophoresis in sodium dodecylsulfate (SDS-PAGE) and subsequent silver staining.

3. Preparation of Recombinant Interferon alpha (rIFNα)

a. Preparation of a DNA Expression Vector for an IFNα Fusion Protein

A recombinant DNA molecule (rDNA) designated pCMV-IFN was prepared that expresses a recombinant interferon alpha (rIFNα) protein. This protein is a fusion protein having an amino acid residue sequence shown in FIG. 2, including an amino terminal portion corresponding to a portion of placental alkaline phosphatase from residue 1 to residue 69, and having a carboxy terminal portion corresponding to IFNαA from residue 70 to residue 219. pCMV-IFN includes a DNA segment having the nucleic acid sequence shown in FIG. 2.

For the preparation of pCMV-IFN, a DNA segment that encodes the IFNα portion and including the nucleotide base residue sequence from base 254 to base 703 shown in FIG. 2 was isolated from a cDNA clone provided by P. Gray. The isolated IFNα encoding DNA segment was then combined into the eucaryotic expression vector pCMVhyg (obtained from H. Karasuyama) so as to operatively link the IFNα coding DNA segment with a DNA segment that encodes an aminoterminal portion of alkaline phosphatase having the nucleotide base residue sequence from base 47 to base 253 shown in FIG. 2, thereby forming pCMV-IFN. The resulting rDNA molecule, pCMV-IFN, encodes and expresses an alkaline phosphatase-IFNα fusion protein having the amino acid residue sequence shown in FIG. 2 from amino acid residue 1 to residue 219, and is referred to as IFNα protein.

b. Purification of IFNα Protein.

pCMV-IFN, prepared in Example 3a, was introduced into murine L cells by the calcium phosphate method, and successfully transfected L cells were isolated by selection for hygromycin resistance conferred by genetic markers present in the vector pCMV-IFN. The resulting transfected L cells were grown to confluence in roller bottles. Culture medium in the roller bottles was then replaced with Iscove's serum substituted medium containing huTransferrin (18 μg/ml), BSA (100 μg/ml) and hygromycin B (500 μg/ml), and the confluent L cells were maintained under normal culture conolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such as $^{111}$ indium or $^3H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3-46 (1981). The techniques of protein conjugation or coupling through activated functional groups are particularly applicable. See, for example, Aurameas, et al., Scand. J. Immunol., 1:7-23 (1978), Rodwell et al., Biotech., 3:889-894 (1984), and U.S. Pat. No. 4,493,795.

The diagnostic systems can also include, preferably as a separate package, a specific binding agent. A "specific binding agent" is a molecular entity capable of selectively binding a reagent species of the present invention but is not itself a protein expression product, polypeptide, or polypeptide conjugate or aggregate of the present invention. Exemplary specific binding agents are antibody molecules, complement proteins or fragments thereof, protein A, and the like. For detecting CR2 ligand, the specific binding agent can bind the anti-CR2 ligand antibody molecules of this invention when it is present as part of an immunocomplex. When detecting patient anti-CR2 antibodies, anti-human Fc antibodies are conveniently used. In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the presence or quantity of CR2 ligand or anti-CR2 ligand antibodies in a body fluid sample such as blood serum, plasma or urine. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites, et al, published by Lange Medical Publications of Los Altos, Calif. in 1982, and in U.S. Pat. Nos. 3,654,090; 3,850,752; and 4,016,043, which are all incorporated herein by reference. Thus, in preferred embodiments, the CR2 ligand or an anti-CR2 ligand antibody molecule of the present invention can be affixed to a solid matrix to form a solid support that is separately packaged in the subject diagnostic systems.

The reagent is typically affixed to the solid matrix by adsorption from an aqueous medium although other modes of affixation, well known to those skilled in the art can be used.

Useful solid matrices are well known in the art. Such materials include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microliter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. The term "package" refers to a solid matrix or material such as gloss, plastic, paper, foil and the like capable of holding within fixed limits a diagnostic reagent such as a polypeptide, antibody or monoclonal antibody of the present invention. Thus, for example, a package can be a glass vial used to contain a contemplated diagnostic reagent or it can be a microtiter plate well to which microgram quantities of a contemplated diagnostic reagent have been operatively affixed, i.e., linked so as to be capable of being immunologically bound by an antibody or CR2 ligand to be detected.

2. Diagnostic Methods

The present invention also contemplates any diagnostic method that results in detecting CR2 ligand or anti-CR2 ligand antibodies in a body fluid sample using CR2 ligand or antibody molecule-containing compositions of this invention. Thus, while exemplary methods are described herein, the invention is not so limited.

To detect the presence of a CR2 ligand in a patient, a bodily fluid sample such as blood, plasma or serum from the patient is contacted by admixture under biological assay conditions with an anti-CR2 ligand antibody molecule of the present invention to form an immunoreaction admixture. The admixture is then maintained for a period of time sufficient to allow the formation of a CR2 ligand-antibody molecule immunoreaction product (immunocomplex). The complex can then be detected as described herein. The presence of the complex is indicative of CR2 ligand in the sample.

In one embodiment, the detection of CR2 ligands in a body sample is utilized as a means to monitor the fate of therapeutically administered CR2 ligands according to the therapeutic methods disclosed herein.

In a related embodiment for detecting the presence of anti-CR2 ligand antibodies in a patient, the above procedure is followed except that a CR2 ligand of the present invention is admixed with a patient's bodily fluid sample to form the immunoreaction admixture. The presence of an immunoreaction product is indicative of anti-CR2 ligand antibodies in the sample.

In preferred embodiments the diagnostic methods of the present invention are practiced in a manner whereby the immunocomplex is formed and detected in ditions. Culture medium supernatants were harvested every 24 hours and used as a source of IFNα protein. Under this regimen, steady IFNα protein production was observed for five days. The collected supernatants from five days culturing were pooled and the IFNα protein in pooled supernatants was precipitated with ammonium sulfate. The precipitated IFNα protein was collected, suspended in 0.1M potassium phosphate buffer, pH 6.0, containing 10% glycerol and dialyzed with 1000 volumes of the same buffer for 12 hours at 4C. The dialyzed precipitate was chromatographed on a P60 column to form separate dimeric and monomeric IFNα fractions. Monomeric IFNα fractions were pooled and passed over a horse anti-human IFNα affinity column to yield homogeneous affinity purified active IFNα protein. Of eleven IFNα-secreting, hygromycin-resistant clones, the best producer (clone LI-3) yielded 150 μg of IFNα fusion per liter in a 24 hr growth period as assessed by the IFNα-specific ELISA described below in Example 3c. The affinity purified IFNα protein so produced from clone LI-3 is referred to as affinity-purified recombinant IFNα (rIFNα).

c. Detection of Recombinant IFNα by ELISA

Various amounts of affinity-purified recombinant IFNα(rIFNα) prepared in Example 3b was added to the wells of Falcon EIA plates in 50 μl of coupling buffer (100 mM NaHC03, pH 9.3) and maintained for 2 hours at 37° C. to allow the IFNα to absorb onto the walls of the wells. Subsequently, the wells were washed by 3-fold immersion in PBS containing Tween 20 at 0.05% (referred to as PBST) and then PBST was added to the wells and the wells were maintained for 1 hour at 37° C. as a saturation step. After the wash and saturation steps, twice-affinity-purified CR2, prepared as described in Example 2, was added to each well in about 50 ul of PBST to form a binding reaction admixture containing 50 nanograms (ng) the amount of CR2 per 50 ul. The admixture was maintained for 2 hours at 37° C. to allow the added CR2 in the liquid phase to specifically bind with the rIFNα present immobilized in the solid phase on the walls of the wells. The wells were then washed with PBST to remove unbound CR2. Thereafter, the washed wells were incubated (admixed and maintained) successively for 1 hour at room temperature first with monoclonal anti-CR2 antibody HB5 (50 ng in 50 μl PBST/well) and then with rabbit anti-mouse antibody conjugated to alkaline phosphatase (50 μl of a 1:1000 solution in PBST/well), the wells being washed with PBST after each incubation. A chromogenic alkaline phosphatase substrate (100 μg p-nitrophenyl phosphate dissolved in 100 μl, 150 mM NaCl, 50 mM Tris-HCl, pH 8.5) was added to each well and the wells maintained for 60 minutes at 37° C. to allow for the formation of p-nitrophenol as a means to detect the amount of immunoreaction product formed, and thereby the amount of specific CR2 binding to IFNα in the solid phase. The formation of p-nitrophenol was determined by measuring optical absorbance at 405 nm in a Titertek ELISA reader (Titertek Multiskan MCC/340, Metea, Va.). Table 3 shows the results of the above detection of CR2 binding to rIFNα in the solid phase as determined by ELISA.

TABLE 3

Binding of CR2 to IFNα

| Concentration of IFNα (ug/ml) | Binding |
|---|---|
| .25 | 0.1 |
| 2.5 | 0.2 |
| 5.0 | 0.3 |
| 10.0 | 0.55 |
| 15.0 | 0.9 |

The data in Table 3 shows that the amount of binding, expressed in units of absorbance when measured at 405 nm, is dependent on the amount of CR2 added to the solution. When control protein bovine serum albumin (BSA) was added to the binding reaction admixture in place of CR2, no dose dependent binding was observed indicating that the interaction between CR2 and rIFNα is a specific binding interaction.

d. Preparation of rIFNα Compositions Containing At Least Two CR2 Binding Sites rIFNα prepared in Example 3b is provided in a solution of PBS at a concentration of about 0.1 mg/ml. The solution is maintained at 23° C. for 120 minutes to allow air oxidation to drive an oxidizing reaction between cysteine residues present in rIFNAα and form conjugates of rIFNα protein having disulfide bridges formed between rIFNα protein molecules. The resulting solution contains an rIFNAα composition having at least two CR2 binding sites per conjugate.

4. Preparation of Interferon Containing a Modified CR2 Binding Site

The DNA segment that encodes the rIFNα protein according to Example 3a is subcloned into the plasmid pBluescript (Stratagene Cloning Systems, San Diego, Calif.). Sac1 and BamH1 restriction endonuclease sites are introduced adjacent to the CR2 binding site coding DNA sequence shown in Step I of FIG. 2 by site-directed mutagenesis using two mismatch primers according to the scheme shown in FIGS. 3A and 3B. By mutagenesis of the nucleotide at position 469, the base A is changed to a base G to create a Sac1 endonuclease site. By similar mutagenesis of the nucleotide at position 504, the base T is converted to base a G and at the nucleotide position 508, the base A is converted to a base C. These latter two changes create a BamH1 endonuclease site as shown in FIG. 3. The resulting rDNA molecule containing the substituted bases and encoding rIFNα is then cleaved with Sac1 and BamH1 restriction endonucleases to allow for removal of the DNA segment encoding the CR2 binding site portion of rIFNα. A 41 base long single-stranded oligonucleotide, having the oligonucleotide sequence shown in Step II of FIG. 3B and coding for the synthetic polypeptide including the amino acid residue sequence QLYNVEA, is annealed to the overhangs present on the rDNA molecule generated by the Sac1 and BamH1 restriction cuts to form a DNA segment encoding a modified rIFNα having a CR2 binding site amino acid residue sequence as shown in FIG. 3B. The modified rIFNα-encoding DNA segment is removed from the plasmid pBluescript by digestion with the restriction enzymes Not1 and Xho1 and ligated into the Not1/Xho1 restriction sites of the predigested expression plasmid pCMVhyg to form pCMV-mIFNα. The expression plasmid pCMV-mIFNα expresses an IFNα having a modified CR2 binding site, which site includes the amino acid residue sequence —QLYNVEA—. pCMV-mIFNα is then transfected into mouse L cells as described in Example 3b to produce an IFNα having a modified CR2 binding site.

5. Anti-CR2 Ligand Antibodies a. Preparation of Antibodies

Synthetic polypeptides related to the CR2 ligands C3 or CBP-A having the sequence of polypeptides p7 and p9 from Table 2 were independently conjugated to bovine serum albumin (BSA) at an equal weight ratio using the glutaraldehyde coupling procedure of Aurameas et al. (*Scand. J. Immunol.*, 1:7-23, 1978). New Zealand white rabbits were injected with an immunogen comprising 2.5 mls of a PBS suspension containing 1.25 mls complete Freund's adjuvant and 0.5 mg of polypeptide in the form of polypeptide-BSA conjugate. Thereafter, each rabbit was boosted with the same immunogen 7, 14, and 21 days after the first immunization except that incomplete Freund's adjuvant was used. About 28 days after the first immunization, antisera was collected from the immunized rabbits and analyzed in the ELISA assay described in Example 5b to detect anti-CR2 ligand antibody immunoreactivity.

b. ELISA Measurement of Anti-Polypeptide Antibody Immunoreactivity

About 5-10 ng of the synthetic polypeptides p7, pB, p9, p2, p6 and p10 representing diverse CR2 ligands and prepared in Example 1, or rIFNα prepared in Example 3b were absorbed to wells of Falcon EIA plates as described in Example 3c. After washing and saturating the plates with PBST, about 50 μl of a 1:1000 dilution of anti-polypeptide antisera prepared in Example 5a was added to each well to form an immunoreaction admixture containing a CR2 ligand in the solid phase, and an anti-CR2 ligand antibody in the liquid phase. The immunoreaction admixture was then maintained for 2 hours at 37° C. to allow a first immunoreaction product to form. The wells were then washed with PBST to remove unbound antibodies. Fifty ul of a solution containing goat anti-rabbit alkaline phosphatase conjugate (Jackson Labs, 1:1000 solution in PBST) was added to each well to form a second immunoreaction admixture, and the admixture was maintained at room temperature to allow a second immunoreaction product to form. The wells were washed with PBST and the second immunoreaction product was detected using a chromogenic substitute as described in Example 3c. The immunoreactivity of the anti-CR2 ligand antibody preparations are shown below in Table 4.

TABLE 4

| Immunoreactivity of Anti-CR2 Ligand Antibodies With Diverse CR2 Ligands | | | |
|---|---|---|---|
| Source of Polypeptide Sequence | Solid Phase Antigen | Anti-CR2 Ligand Immunoreactivity | |
| | | p7 | p8 |
| C3 | p7 | 1.0 | 1.0 |
| CBP-A | p8 | 1.1 | 1.0 |
| CBP-B | p9 | 0.3 | 0.3 |
| IFNαA | p2 | 0.3 | 0.2 |
| IFNαF | p6 | N.T. | 0.2 |
| IFNαA | rIFNα | 1.2 | 1.2 |
| Fibronectin | p10 | 0.1 | 0.1 |

As shown in Table 4, the anti-polypeptide antisera prepared against the CR2 ligands p7 or p8 each immunoreacted with their homologous immunizing peptide and also immunoreacted to varying degrees with several other polypeptides bearing a CR2 binding site. These same antisera did not contain polyclonal antibody molecules that significantly immunoreacted with a fibronectin fragment-derived polypeptide (p10) indicating the specificity of the immunoreaction. The anti-CR2 ligand antibodies also immunoreacted strongly with the rIFNα prepared in Example 3b. This latter immunoreaction demonstrates that native IFNαA contains a structural domain (i.e., a CR2 binding site) that cross-reacts with antibodies immunoreactive with the CR2 ligands of this invention.

6. Direct Binding of CR2 to CR2 Ligands

About 5-10 ng of synthetic polypeptides related to the CR2 ligands C3, CBP-A, CBP-B, IFNαA, and IFNαF, and a control protein, fibronectin, (peptides p7, p8, p9, p2, p6 and p10, respectively and prepared in Example 1) were absorbed to wells of Falcon EIA plates according to the method described in Example 3c to form solid phase CR2 ligand. Following wash and saturation steps with PBST, a PBST solution (50 μl) containing about 100 ng of affinity-purified CR2, prepared as described in Example 2, was added to each well to form a first admixture and maintained for 2 hours at 37° C. to allow the CR2 in solution to specifically bind to the solid phase CR2 ligand. Following removal of unbound CR2 with a PBST wash, wells were incubated successively for 1 hour at room temperature first with HB5 monoclonal anti-CR2 antibodies (50 ng/well) followed with rabbit anti-mouse antibody conjugated to alkaline phosphatase (50 μl of a 1:1000 solution in PBS). The incubations, washes and colorimetric detection of immunoreaction product were performed as described in Example 3c. The detection of an immunoreaction product is shown below in Table 5 and indicates that the CR2 in solution specifically binds to the solid phase CR2 ligands.

TABLE 5

| Direct Binding of CR2 to CR2 Ligands | | |
|---|---|---|
| Source of Polypeptide Sequence | Solid Phase Ligand | Binding Reactivity |
| C3 | p7 | 1.00 |
| IFNαA | p2 | 0.32 |
| IFNαF | p6 | 0.15 |
| CBP-A | p8 | 0.48 |
| CBP-B | p9 | 0.38 |
| Fibronectin | p10 | 0.10 |

CR2 binds with synthetic polypeptides related to the CR2 binding site of C3, IFNαA, CBP-A and CBP-B. These data demonstrate that the CR2 ligands of this invention, and other CR2 ligands, when used in a solid-phase binding assay, specifically interact (bind) with synthetic polypeptides derived from IFNαF (p6) or fibronectin fragments (p10). These latter data are consistent with the observations on the effects of CR2 ligands on B cell proliferation as discussed below in Example 8.

7. Inhibition of CR2 Binding to Native CR2 Ligands Using CR2 Ligand Polypeptides A binding reaction admixture containing rIFNα in the solid phase and CR2 in the liquid phase was prepared as described in Example 3c except that a competing CR2 ligand shown in Table 6 was also included in the admixture at a concentration of 100ug/ml. Thereafter, the binding assay was conducted as described in Example 3c to measure the amount of CR2 specifically bound to rIFNα. The results of inhibition of CR2 binding to rIFNα by CR2 ligand polypeptides is shown in Table 6.

TABLE 6

Inhibition of CR2 Binding to rIFNα Using CR2 Ligand Polypeptides

| Source of Polypeptide Sequence | Inhibitor Polypeptide | Inhibition of Binding (%) |
|---|---|---|
| N.A. | none | 0 |
| IFNαA | p2 | 48 |
| IFNα88 | p4 | 45 |
| C3 | p7 | 50 |
| IFNαF | p6 | 0 |
| Fibronectin | p10 | 0 |

The data in Table 6 indicates that CR2 ligands such as the polypeptides used above can inhibit the specific binding of CR2 to a native CR2 ligand such as the indicated interferon alpha species that bind CR2. Similar results were obtained when purified EBV gp350/220 protein was used in the liquid phase in place of CR2, indicating that CR2 ligands inhibit EBV binding to CR2.

8. Inhibition of B Lymphocyte proliferation

A B cell proliferation assay system was used to examine the ability of various CR2 ligand polypeptides to inhibit B lymphocyte proliferation. Cultures of the cell lines shown in Table 7 were established at a density of $2\times10^4$ cells per well of a 96 well microtiter plate in serum-free ISCOVE's medium. Varying amounts (zero to 500 μg per ml of culture) of the polypeptides of Table 6 were added to the cultures, and the cell-polypeptide admixtures maintained for 24 to 48 hours at 37° C. Thereafter, 1 μCi of $^3$H-thymidine label was admixed with each culture and maintained for 4 hours at 37° C. to allow for label incorporation into proliferating cells. After 4 hours, the cultures were harvested and the incorporated label measured by standard techniques. The results of the above assay procedures are shown in Table 7.

TABLE 7

CR2 Ligand Polypeptides Inhibit[b] B Cell Proliferation

| | Human | Murine | | | |
|---|---|---|---|---|---|
| EBV-Induced[a] Polypeptides[c] | B cell Peripheral B cell | LPS-induced Lymphoma Raji | splenic B Cell | B cell Lymphoma A20, | 38C13 |
| p7 QLYNVEATS | + | ++ | ++ | + | + |
| p2 QLNDLEACV | +++ | +++ | +++ | +++ | +++ |
| p4 QLNNLEACV | +++ | +++ | N.T.[d] | +++ | +++ |
| p5 QMNDLEACV | — | — | N.T. | — | — |
| p6 QLNDMEACV | — | — | N.T. | — | — |
| Control Peptides: | | | | | |
| p10 SPGRGD | — | — | — | — | — |
| p11 GRGDSP | — | — | — | — | — |

[a]Each cell line was cultured as described in Example 8 with the following exceptions: human peripheral B cells were cultured with EBV (strain 895/8) at a multiplicity of infection excess of 1.0 EBV units per cell and was admixed simultaneously with admixture of polypeptide; mouse splenic B cells were cultured with the admixed polypeptides in combination with lipopolysaccharide (LPS) at 25 μg per ml.
[b]Inhibition is expressed as the amount of added polypeptide required to exhibit half-maximal inhibition —: no inhibition at 500 μg polypeptide per ml; +: half-maximal inhibition at 200-500 μg/ml; ++: at 50-200 μg/ml; +++: at 5-50 μg/ml.
[c]Polypeptides were prepared as described in Example 1.
[d]N.T. indicates not tested.

The results in Table 7 show that synthetic polypeptides p7, p2 and p4, derived from C3, IFNαA and IFNα88, respectively, inhibited B cell growth in all assays used. Inhibition is unlikely due to nonspecific toxicity because the fibronectin-derived polypeptides used as controls did not inhibit proliferation. Additionally, none of the polypeptides tested inhibited proliferation of human (HSB2) or murine (BW5147) T cell lymphomas (cell lines known to lack CR2 receptors).

The inhibition of the EBV-induced B cell proliferation by the CR2 ligand polypeptides derived from the CR2 binding sites of IFNαA and IFNα88 corroborates our receptor binding studies (Examples 6 and 7), which demonstrated that rIFNα and other CR2 ligands bind to the same area on CR2. The data indicate that CR2 ligand polypeptides not only bind affinity-purified CR2 in a solid-phase assay, but also bind native CR2 in the plasma membrane.

9. Inhibition of Direct Binding of CR2 Ligands to Native CR2

Fresh blood was collected from a healthy donor, maintained at room temperature for 2 hours, centrifuged at 2000×g for about 10 min and the resulting supernatant collected. Five mg of Zymosan A particles (Sigma Chemical Co., St. Louis, Mo.) were boiled for 30 min in 20 ml of 150 mM NaCl and washed three times in phosphate-buffered saline (PBS) to form activated particles. One mg of activated particles was admixed with 0.5 ml of the collected blood supernatant, the admixture was maintained at 37° C. for 30 minutes, and then the particles were washed 3 times in PBS. The washed particles were re-suspended in PBS at a concentration of 0.5 mg/ml to form a C3-coated Zymosan composition.

Cultures containing $10^5$ Raji cells were admixed with 100 microliters (μl) of culture medium containing varying amounts (zero to 200 μg) of C3 or IFNαA derived polypeptides (p7 and p2 prepared in Example 1) or rIFNα prepared in Example 3b and the admixture maintained at 37° C. for 30 minutes to allow the CR2 ligand polypeptides to bind any CR2 receptor present on the Raji cells. Thereafter, 50 μl of the C3-coated Zymosan composition were added to each cell culture. The cell cultures were centrifuged for 1 minute at 600 g and incubated at 37° C. for 30 minutes. The cell cultures were then washed with prewarmed culture medium to rinse non-bound particles off of the cells. Washed cells were observed using a microscope to detect the bound particles, and count the number of particles that were attached per cell in the form of rosettes. More than 3 rosettes per cell were counted as C3 specific binding. Inhibition is expressed as the percent decrease in bound rosettes when comparing binding in the presence or absence of admixed polypeptide. The results show that C3 and IFNαA derived polypeptides (p7 and p2) and rIFNα inhibited rosette formation (See Table 8 below).

TABLE 8

| Derived Polypeptide | Percent Inhibition of Zymosan-C3 Rosette Formation in Raji Cells |
| --- | --- |
| p7 (C3) | 77 |
| p2 (IFNαA) | 55 |
| rIFNα | 35 |

These are significant results, because they show that the CR2 ligands p7, p2 and rIFNα can assume conformations which competitively inhibit direct binding of the CR2 ligand C3 to native CR2 present on Raji cells.

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. A CR2 ligand consisting of a polypeptide selected from the group consisting of:
QLNDLEA,
QLNDLEAC,
QLNDLEACV,
QLNDLEACVI,
QLNDLEACVIQ,
QQLNDLEA,
YQQLNDLEA,
LYQQLNDLEA,
QLNNLEA,
QLNNLEAC,
QLNNLEACV,
QLNNLEACVI,
QLNNLEACVIQ,
QQLNNLEA,
YQQLNNLEA, and
LYQQLNNLEA, said ligand being capable of specifically binding to CR2.

2. CR2 ligand consisting of a polypeptide selected from the group consisting of:
QNNDVEATS,
QLNDVEATS,
QLNNVEATS,
QLNNLEATS,
QSNGVEALT,
QNSGLEALT,
QNSGLEALI,
QSNGVEALI,
NSVGEALI,
QNAIVEALI, and
QNAIVEALT,
ligand being capable of specifically binding to CR2.

* * * * *